United States Patent [19]
Conrad et al.

[11] Patent Number: 5,824,803
[45] Date of Patent: Oct. 20, 1998

[54] COMPOUNDS LABELED WITH CYANATE OR THIOCYANATE METAL COMPLEXES FOR DETECTION BY INFRARED SPECTROSCOPY

[75] Inventors: David W. Conrad, Alexandria, Va.; Charles H. Patterson, Jr., Laurel, Md.

[73] Assignee: The United States of America as represented by the Secretary of the Navy, Washington, D.C.

[21] Appl. No.: 940,736

[22] Filed: Sep. 30, 1997

[51] Int. Cl.$^6$ .............. C07F 231/12; C07F 293/04; C07D 231/12
[52] U.S. Cl. .............. 548/109; 548/101; 548/107
[58] Field of Search .................. 548/339.1, 109, 548/107, 101

[56] References Cited

U.S. PATENT DOCUMENTS

| | | | |
|---|---|---|---|
| 4,656,142 | 4/1987 | Jaouen et al. | 436/501 |
| 4,983,646 | 1/1991 | Jaouen et al. | 552/630 |
| 5,578,499 | 11/1996 | Ismail et al. | 436/524 |

*Primary Examiner*—Joseph McKane
*Assistant Examiner*—Ebenezer Sackey
*Attorney, Agent, or Firm*—Thomas E. McDonnell; Ralph T. Webb

[57] ABSTRACT

A labeled compound detectable by IR spectroscopy contains at least one histidine residue bound to a cyanate or thiocyanate metal complex that has an IR absorption band within the spectral region of 2399-1900 cm$^{-1}$. An assay reagent for simultaneously detecting or determining a plurality of different analytes in a sample is made up of a plurality of different labeled compounds, each being independently distinguishable from the others by absorbing energy in a different and distinguishable region in the range of 2300 to 1900 cm$^{-1}$.

3 Claims, 2 Drawing Sheets

COMPOUNDS LABELED WITH CYANATE OR THIOCYANATE METAL COMPLEXES FOR DETECTION BY INFRARED SPECTROSCOPY

BACKGROUND OF THE INVENTION

1. Field of the Invention

The invention relates to labeled compounds for detection by infrared spectroscopy and in particular to compounds labeled with cyanate or thiocyanate metal complexes that are detectable in the energy region of 2300-1900 cm$^{-1}$.

2. Description of the Related Art

Labeled compounds are used in assays for the detection and quantitation of molecular species. Types of labels that have been used include radioisotopes, enzymes, and fluorescent and phosphorescent compounds. Each of these types of labels has disadvantages. For example, radioisotopes have a limited half-life, and special precautions must be taken in their storage, use and disposal. Enzyme labels can be bulky and can interfere with binding reactions in assays. Moreover, enzymes are susceptible to denaturation and inhibition. Fluorescent labels may be prone to photobleaching or to fluorescence quenching if used near a metal or semiconductor surface. In addition, the fluorescent signal from a labeling molecule may be subject to interference due to fluorescence by the sample or by parts of the matrix or environment surrounding the sample. Moreover, commonly used fluorescent molecules are often difficult to attach to analytes, and, because they are often large molecules, they may change the properties of the analyte.

Recently, molecules that absorb energy in the infrared region of the spectrum have been developed as labels. Metal carbonyl complexes have been used as infrared-active dyes, and a technique called carbonylmetalloimmunoassay (CMIA) has been developed for using the carbonyl dyes in immunoassays. See, for example, U.S. Pat. No. 5,578,499 to Ismail, U.S. Pat. No. 4,656,142 to Jaouen et al, U.S. Pat. No. 4,983,646 to Jaouen et al, V. Philomin et al, "New Applications of Carbonylmetalloimmunoassay (CMIA): a Non-Radioisotopic Approach to Cortisol Assay" Journal of Immunological Methods, 171 (1994) pp 201–210, Samain et al "Carbonylmetalloimmunoassay (CMIA) a New Type of Non-Radioisotopic Immunoassay" Journal of Immunological Methods, 148, (1992) pp 65–75, Salmain et al "Fourier Transform Infrared Spectroscopic Method for the Quantitative Trace Analysis of Transition-Metal Carbonyl-Labeled Bioligands" Analytical Chemistry, vol 63, No. 20, Oct. 15, 1991, Wang et al, "Metal Carbonyl Labels for Oligonucleotide Analysis by Fourier Transform Infrared Spectroscopy", J. Am. Chem. Soc. 1993, 115, pp 4399–4400, Salmain et al "Use of Fourier Transform Infrared Spectroscopy for the Simultaneous Quantitative Detection of Metal Carbonyl Tracers Suitable for Multilabel Immunoassays" Analytical Biochemistry 208, (1993) pp 117–120 (all of the above patents and articles are incorporated herein by reference). Metal carbonyls have the property that they absorb energy very intensely in the region of 2000 to 1800 cm$^{-1}$, a region of the spectrum that is relatively free of interferences from biological molecules and absorbances of H$_2$O. However, metal carbonyls are unstable and tend to decompose quickly, especially when exposed to air or moisture.

SUMMARY OF THE INVENTION

Accordingly, it is an object of the invention to provide labeled compounds that absorb in the spectral region of 2300- 1900 cm-1.

It is a further object of the invention to provide a label for compounds that is relatively small in size so that it does not interfere with the binding of the labeled compound.

It is a further object of the invention to provide a label for compounds that is stable for a relatively long period of time.

It is a further object of the invention to provide a label for compounds that binds readily to histidine residues of the compound.

It is a further object of the invention to provide a method of carrying out a plurality of assays simultaneously by using a plurality of labeled compounds that each absorb energy in a different and distinguishable band of the spectral region of 2300 to 1900 cm$^{-1}$.

These and other objects are attained by providing a labeled compound having at least one histidine residue bound to a cyanate or thiocyanate metal complex that has an IR absorption band within the spectral region of 2300 to 1900 cm$^{-1}$.

DETAILED DESCRIPTION OF THE PREFERRED EMBODIMENT

Figure 1:
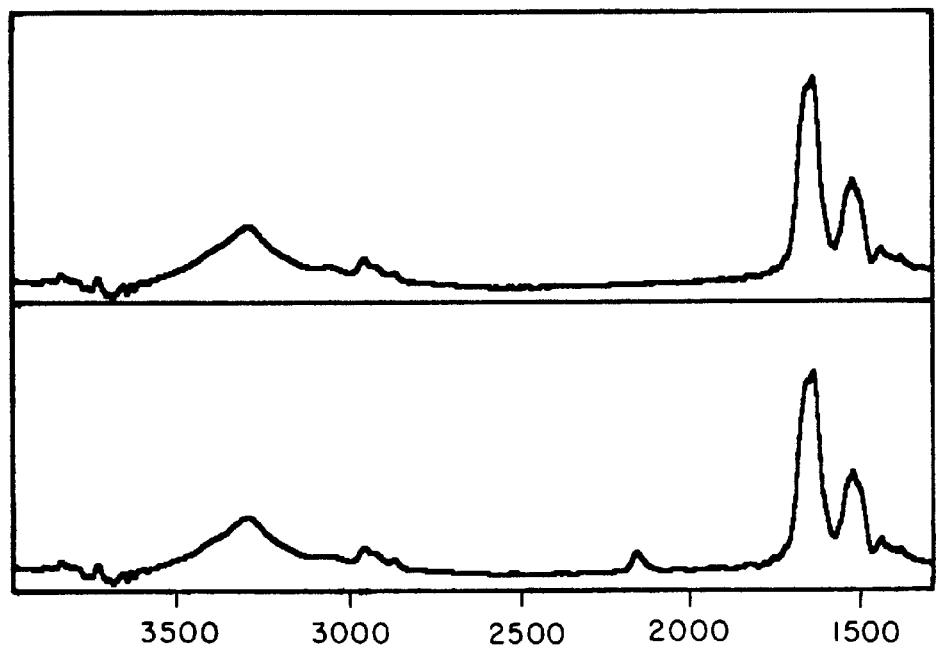
FIGS. 1(a) and 1(b) are the comparative IR spectra of palladium tetrathiocyanate labeled goat IgG and native goat IgG.

The invention relates to labeled compounds having at least one histidine residue bound to a cyanate or thiocyanate metal complex that has an IR absorption band within the spectral region of 2300 to 1900 cm$^{-1}$. The compound can be any compound for which it would be useful to have a label for detecting the compound in an assay. Examples of useful compounds include antibodies, enzymes, nucleic acids (DNA OR RNA), genetically engineered proteins or peptides, ligands for cell surface receptors, hormones, antibiotics, drugs, antigens, fluorescent molecules, phosphorescent molecules, luminescent molecules, chemiluminescent molecules, bioluminescent molecules, lanthanides, actinides, metal chelators, inorganic metal complexes, redox-active metal complexes or organic compounds, and inorganic or organic catalysts. The invention is particularly useful for compounds such as a proteins that already contain histidine residues, but any compound that can be modified by any known means to include a histidine residue may be used. For example, strands of DNA or RNA can be chemically modified by means known in the art to attach histidine residues.

Any transition metal ion that is capable of forming a complex with cyanate or thiocyanate and that is capable of binding or complexing with a histidine residue may be used to form the metal complex. Preferably, the transition metal ion is palladium, platinum, nickel or cobalt. Most preferably, the transition metal ion is palladium.

The labeling of a compound is accomplished by forming a cyanate or thiocyanate metal complex by any means known in the art and then combining the metal complex with the compound to be labeled so that the metal complex binds with nitrogens on the histidine residues of the compound. For example, to form a thiocyanatopalladate-labeled compound, potassium tetrathiocyanatopalladate (II) is formed by reacting potassium thiocyanate with palladium (II) tetrachloride according to the following reaction scheme:

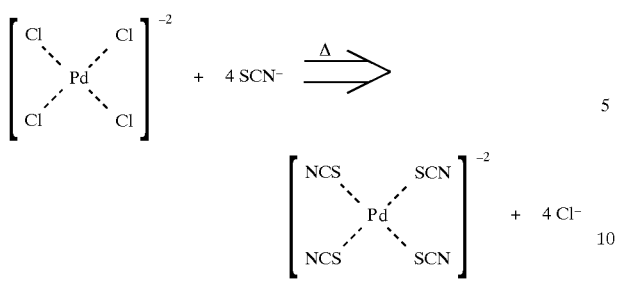

Next, the palladium complex is mixed with the compound to be labeled under conditions that allow the palladium complex to bind to the histidine residues of the compound to be labeled, according to the following reaction scheme:

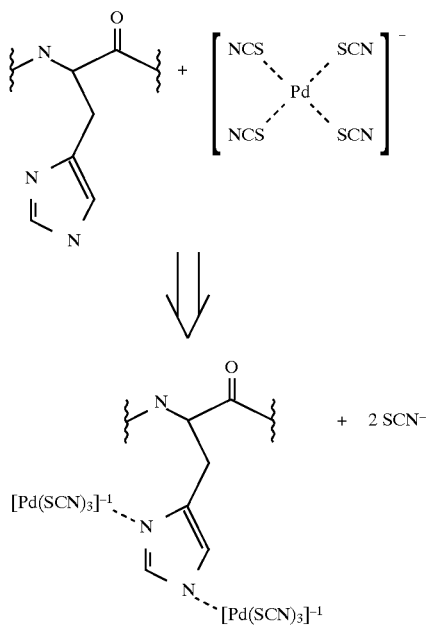

The amount of metal complex that is mixed with the compound to be labeled depends upon the number of histidine residues that the compound contains. For example, if a compound that contains only one histidine residue is to be labeled, the molar ratio of metal complex to the compound should be less than 2:1. For proteins, which typically contain many histidine residues, the molar ratio of metal complex to protein may be as high as about 20:1. At higher ratios, some protein precipitation occurs.

After the labeling reaction is completed, any unbound label and the free thiocyanate released by the complexation reaction with histidine may be removed by gel filtration chromatography.

The labeled compounds of the present invention may be used in place of metal-carbonyl labeled compounds or in place of fluorescent-labeled compounds in assays known in the art. The presence and quantity of a labeled compound in an assay can be determined by detecting its IR absorption band within the spectral region of 2300 to 1900 $cm^{-1}$.

A plurality of different labels having different absorption wavelengths may be created by selecting various different combinations of transition metal ions and cyanate or thiocyanate ligands. By combining different analytes each having a different label, an assay reagent may be created for conducting a plurality of assays at one time.

Having described the invention, the following examples are given to illustrate specific applications of the invention, including the best mode now known to perform the invention. These specific examples are not intended to limit the scope of the invention described in this application.

EXAMPLE 1

Synthesis of Potassium Palladium Tetrathiocyanatopalladate (II)

1.2 g (12.2 mmol) of potassium thiocyanate was dissolved in ethanol and to this solution was added 1.0 g (3.1 mmol) of palladium (II) tetrachloride. The mixture was heated and stirred to speed up the dissolution process. The hot dark red solution was filtered to remove any insoluble material. Crystals were allowed to form in the cooling mother liquor as the solvent was concentrated under a stream of dry nitrogen. The dark red needles were removed from the mother liquor and washed 3 times with 2 mL portions of ice cold (−4° C.) ethanol, and dried in a oven at 120° C. This yielded 1.0 g (80%) of potassium tetrathiocyanatopalladate (II).

EXAMPLE 2

Labeling of Goat IgG (whole molecule) with Potassium Tetrathiocyanatopalladate (II)

5 mL of a solution of goat IgG (0.1 mg/mL) was treated with 129 µL of a potassium tetrathiocyanatopalladate (II) solution (0.1 µg/µL) and allowed to stir for 5 minutes. The molar ratio of palladium to IgG used in this reaction was 10:1. The unreacted palladium complex was removed by gel filtration chromatography (16×0.8 cm, Sephadex G-25, 50 mM sodium acetate buffer. pH 4.5). Only one peak was observed to elute from the column after 30 minutes. (flow rate 1.0 mL/min) which corresponded to the IgG fraction. This result indicated that at this particular molar ratio all the palladium complex had been coordinated with histidines on the IgG. Further evidence of metal complex binding to IgG was provided using UV/Vis absorbance difference spectroscopy. Upon subtracting a spectrum of unmodified IgG from that of the palladium-labeled protein, the spectrum of the coordinated complex was easily resolved. Furthermore, a spectral shift from 300 to 275 nm was observed and is indicative of palladium binding with histidine.

EXAMPLE 3

Detection of Tetrathiocyanatopalladate (II) Labeled Goat IgG by FT-IR

Goat IgG (0.1 mg/mL in PBS pH 7.4) was treated with a 10:1 molar ratio of potassium tetrathiocyanatopalladate(II) to IgG for one minute. The treated IgG was separated from unreacted palladium complex by size exclusion gel filtration. (G-25 Sephadex, PBS pH 7.4) There was a spectral shift in the labeled complex compared to the unlabeled complex from 310 nm to 270 nm. In addition there was a shift in the IR absorbance of the thiocyanate from a doublet in the free complex at 2090 and 2120 $cm^{-1}$ to 2160 $cm^{-1}$ in the labeled complex. Labeled IgG was allowed to adsorb for one hour onto a silicon wafer that had been sputtered with 5000 Å of aluminum. The antibody solution was then rinsed from the wafer using deionized water and dried with a jet of argon. The infrared spectra of both labeled and native IgG were measured using an FT-IR spectrometer (Magna-IR 750 Series II, Nicolet) equipped with a horizontal grazing angle accessory (Model FT-85, Spectra Tech). The spectra are shown in FIGS. 1(a) and 1(b).

EXAMPLE 4

Binding of Labeled Antibodies With Their Respective Antigens

Glass slides coated with a photoactivatable PEG silane surface were exposed to UV light to activate the silane surface. The slides were irradiated through a 2 mm×2 mm dark field window mask so that only that portion of the slide was exposed and activated. The slides were then rinsed and treated with different IgG solutions. One slide was treated with donkey anti-goat IgG, and another with donkey anti-goat IgG that had been treated with a 10:1 molar ratio of potassium tetrathiocyanatopalladate(II). A third slide was treated with donkey anti-rat IgG and a fourth with donkey anti-rat IgG treated with 10:1 potassium tetrathiocyanatopalladate (II). The slides were incubated for 1 hour with the respective solutions and a reductant (sodium cyanoborohydride). After the hour, the slides were rinsed with deionized water. Both the donkey anti-goat IgG slides and the donkey anti-rat IgG slide treated with the palladium complex were incubated with Cy5-labeled goat IgG (0.1 mg/mL) for 30 minutes. The remaining donkey anti-rat IgG slide was incubated with Cy5-labeled rat IgG. After the 30 minutes, the slides were again rinsed with deionized water and dried under argon. Each slide was imaged with the CCD array and stored via computer. This experiment showed that the palladium-treated IgG was just as active as the untreated IgG and that even after treatment there was no increase in nonspecific protein binding.

EXAMPLE 5

Quantitation of Labeled Antibodies Using Infrared Spectroscopy

Figure 2:
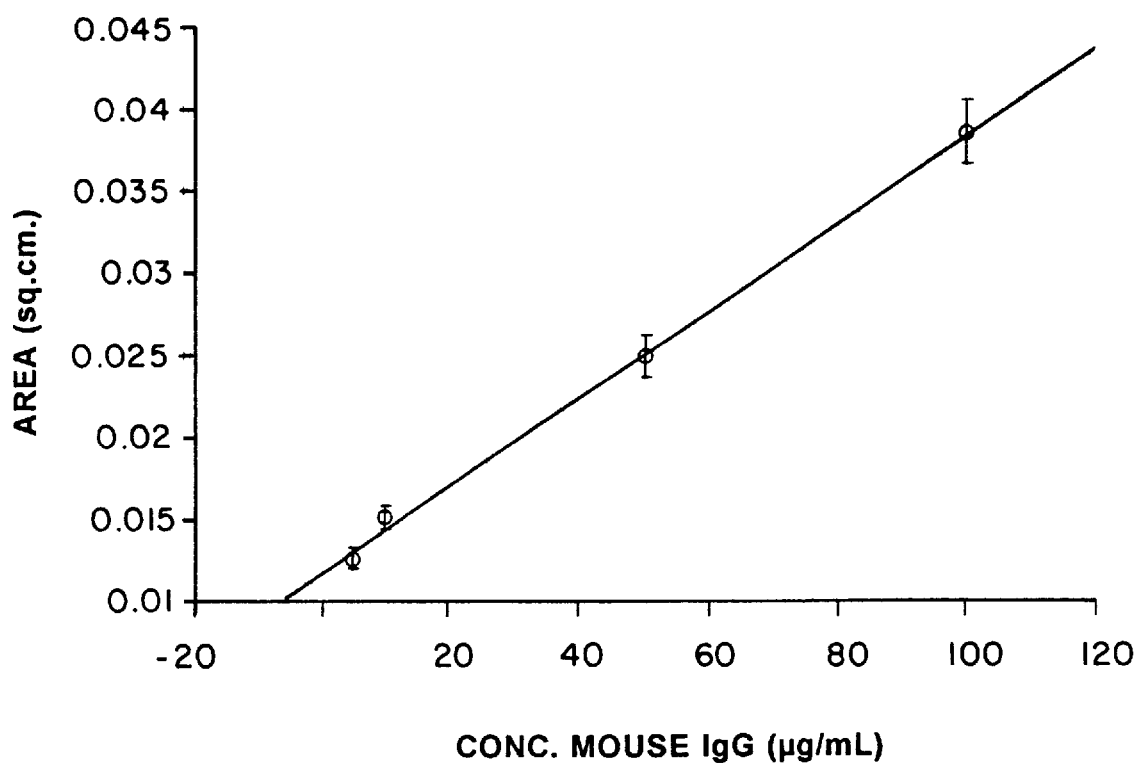
FIG. 2 is a plot of the peak area of the infrared spectrum of labeled mouse IgG in the region of 2200-2100 cm$^{-1}$ vs. the concentration of mouse IgG.

Silicon wafers that had been previously sputtered with aluminum were plasma cleaned. Five wafers were then treated with a solution of rabbit anti-mouse IgG (0.5 mg/mL in PBS pH 7.4) for 60 minutes. Each wafer was rinsed with deionized water and then dried under argon. Different solutions of mouse IgG (100 $\mu$g/mL, 50 $\mu$g/mL, 10 $\mu$g/mL, 5 $\mu$g/mL, 1 $\mu$g/mL and 0 $\mu$g/mL in PBS pH 7.4) that had been labeled with a 20:1 ratio of $K_2Pd(SCN)_4$ to IgG were adsorbed onto each wafer. After a 30 minute incubation with the second labeled antibody, the slides were rinsed with deionized water and dried under argon. The infrared spectrum of each wafer was measured by Fourier transform infrared spectroscopy (FTIR). The area of the peak in the region between 2200-2100 $cm^{-1}$ was integrated by the computer. Although the absorbance maximum of the palladium complex occurs at 2166 $cm^{-1}$, a wide window was used for integration to obtain a sufficient baseline. The area of the peak was plotted versus concentration and the correlation coefficient calculated from the best-fit line was 0.998, indicating a linear relationship between peak area and concentration. The plot is shown in FIG. 2.

Obviously, many modifications and variations of the present invention are possible in light of the above teachings. It is therefore to be understood that, within the scope of the appended claims, the invention may be practiced otherwise than as specifically described.

What is claimed is:

1. A labeled compound comprising a compound having at least one histidine group bound to an metal complex, the metal complex comprising a transition metal ion and at least one cyanate or thiocyanate ligand and the metal complex having an IR absorption band within the spectral region of 2300 to 1900 $cm^{-1}$.

2. The labeled compound of claim 1 wherein the transition metal ion is selected from the group consisting of palladium, platinum, nickel and cobalt.

3. The labeled compound of claim 1 wherein the transition metal ion is palladium.

* * * * *